United States Patent
Brewster et al.

(10) Patent No.: US 11,730,293 B2
(45) Date of Patent: Aug. 22, 2023

(54) DRINK LID ARRANGEMENTS AND METHODS

(71) Applicant: MPD VENTURES, INC., Hillsborough, CA (US)

(72) Inventors: Peter Hollister Brewster, Hillsborough, CA (US); Michael Simons, Hillsborough, CA (US)

(73) Assignee: MPD VENTURES, INC., Hillsborough, CA (US)

( * ) Notice: Subject to any disclaimer, the term of this patent is extended or adjusted under 35 U.S.C. 154(b) by 0 days.

(21) Appl. No.: 16/252,062

(22) Filed: Jan. 18, 2019

(65) Prior Publication Data
US 2020/0229624 A1 Jul. 23, 2020
US 2022/0125227 A9 Apr. 28, 2022

Related U.S. Application Data

(63) Continuation of application No. 14/505,331, filed on Oct. 2, 2014, now Pat. No. 10,226,141, which is a
(Continued)

(51) Int. Cl.
*G08B 21/00* (2006.01)
*A47G 19/22* (2006.01)
(Continued)

(52) U.S. Cl.
CPC ..... *A47G 19/2272* (2013.01); *A47G 19/2227* (2013.01); *A61B 5/082* (2013.01);
(Continued)

(58) Field of Classification Search
CPC ...... B65D 43/02; B65D 25/34; B65D 51/245; B65D 43/0202; A47G 19/22;
(Continued)

(56) References Cited

U.S. PATENT DOCUMENTS 2,003,657 A 6/1935 Stubblefield
5,575,383 A * 11/1996 Seeley ................. B65D 5/4291
206/217
(Continued)

FOREIGN PATENT DOCUMENTS

WO WO-2010021061 A1 * 2/2010 ............. B65D 23/00

OTHER PUBLICATIONS

Notice of Allowance dated Aug. 1, 2014, issued in parent U.S. Appl. No. 12/916,351.

*Primary Examiner* — Toan N Pham
(74) *Attorney, Agent, or Firm* — Squire Patton Boggs (US) LLP

(57) ABSTRACT

An apparatus can include a generally planar portion approximately in a plane. The apparatus can also include a lip portion extending in a direction generally orthogonal to the plane. The generally planar portion is joined to the lip portion at a circumferential edge of the generally planar portion to form a cover for a beverage container. Likewise, a method can include providing contact information on a disposable cover adapted to cover a beverage container. The contact information is not necessarily provided by the manufacturer of the beverage or beverage container. The method can also include receiving contact from a user of the disposable cover. The method can further include coordinating the delivery of a service to the user of the disposable cover responsive to the contact received from the user.

29 Claims, 4 Drawing Sheets

Related U.S. Application Data continuation-in-part of application No. 12/916,351, filed on Oct. 29, 2010, now Pat. No. 8,876,166.

(51) Int. Cl.

| | | |
|---|---|---|
| *B01F 23/23* | (2022.01) | |
| *B01F 31/60* | (2022.01) | |
| *A61B 5/08* | (2006.01) | |
| *A61B 5/1172* | (2016.01) | |
| *A61B 5/145* | (2006.01) | |
| *A61B 5/00* | (2006.01) | |
| *B65D 51/24* | (2006.01) | |
| *B01F 101/17* | (2022.01) | |
| *G07G 1/00* | (2006.01) | |

(52) U.S. Cl.
CPC ........ *A61B 5/1172* (2013.01); *A61B 5/14507* (2013.01); *A61B 5/6887* (2013.01); *B01F 23/238* (2022.01); *B01F 31/60* (2022.01); *B65D 51/245* (2013.01); *A47G 2019/2244* (2013.01); *B01F 2101/17* (2022.01); *G07G 1/0045* (2013.01)

(58) Field of Classification Search
CPC ................ A47G 19/2272; A47G 23/16; A47G 19/2227; G09F 3/02
See application file for complete search history.

(56) References Cited

U.S. PATENT DOCUMENTS

| | | | |
|---|---|---|---|
| 5,738,921 A | 4/1998 | Andersen et al. | |
| 5,894,952 A | 4/1999 | Mendenhall et al. | |
| 5,957,313 A | 9/1999 | Bouan | |
| 5,984,135 A | 11/1999 | Brown | |
| 6,906,295 B2 | 6/2005 | Ge | |
| 7,040,139 B2 * | 5/2006 | Sunshine | G01N 29/022 340/10.1 |
| 7,418,311 B1 * | 8/2008 | Lagassey | G07F 9/026 221/150 R |
| 7,916,034 B1 | 3/2011 | Puccini | |
| 7,950,545 B1 * | 5/2011 | Roberts | A47G 19/2205 220/669 |
| 8,613,417 B2 * | 12/2013 | Kraus, Jr. | G09F 23/08 248/346.11 |
| 9,024,766 B2 * | 5/2015 | Hood | A47G 19/2227 340/603 |
| 9,346,607 B2 * | 5/2016 | Madjar | B65D 83/00 |
| 9,930,980 B2 * | 4/2018 | Pau | A47G 23/16 |
| 10,352,759 B1 * | 7/2019 | Jensen | A01K 7/02 |
| 2005/0178766 A1 | 8/2005 | Washington et al. | |
| 2007/0178284 A1 | 8/2007 | Barry | |
| 2008/0030326 A1 | 2/2008 | Gal | |
| 2008/0190945 A1 | 8/2008 | Milnark | |
| 2009/0047469 A1 | 2/2009 | Lane et al. | |
| 2009/0169419 A1 * | 7/2009 | Hyde | A61L 2/10 422/106 |
| 2009/0239510 A1 | 9/2009 | Sennett et al. | |
| 2009/0242590 A1 | 10/2009 | Saveliev et al. | |
| 2010/0163567 A1 * | 7/2010 | Chiang | G01F 23/686 220/703 |
| 2010/0332420 A1 | 12/2010 | Groening | |
| 2011/0050431 A1 | 3/2011 | Hood et al. | |
| 2011/0139800 A1 | 6/2011 | Urban | |
| 2011/0145739 A1 | 6/2011 | Berger et al. | |
| 2011/0153398 A1 * | 6/2011 | Tjhai | G06Q 20/322 705/14.14 |
| 2011/0238520 A1 * | 9/2011 | Selley | G06Q 30/02 705/26.3 |
| 2012/0204307 A1 | 8/2012 | De Mattei | |
| 2014/0291188 A1 | 10/2014 | Maddox | |
| 2015/0050398 A1 | 2/2015 | Shields | |
| 2015/0122688 A1 * | 5/2015 | Dias | A47G 19/025 206/459.1 |
| 2016/0030900 A1 * | 2/2016 | Jin | A47J 43/0465 261/141 |
| 2018/0078065 A1 * | 3/2018 | Cheatham | A47G 19/2227 |

\* cited by examiner

MARTINI

HIGH BALL

LOW BALL

PINT

WINE

CHAMPAGNE

COGNAC

BEER

SHOT

DRINK LID ARRANGEMENTS AND METHODS

CROSS-REFERENCE TO RELATED APPLICATIONS

The present application is a 37 C.F.R. § 1.53(b) continuation of co-pending U.S. patent application Ser. No. 14/505,331 filed Oct. 2, 2014, now U.S. Pat. No. 10,226,141, which is a continuation-in-part of U.S. patent application Ser. No. 12/916,351, filed Oct. 29, 2010, now U.S. Pat. No. 8,876,166, the entirety of which is hereby incorporated herein by reference.

BACKGROUND

Field

Lids and covers as well as dispatch of services using lids are discussed. Certain embodiments relating to a lid that is configured for various security, privacy, or health purposes.

Description of the Related Art

Various lids for cups have been made. For example, lids for preventing splashing of a contained fluid are described. These lids have a wide variety of characteristics. For example, some lids are disposable lids that have a depressed area for receiving and containing foodstuff such as condiments. Other lids are more durable lids with a slit and vents or other device that permits a child to drink from the cup, while preventing the cup from spilling if the cup is accidentally overturned. Other lids can adhere to the rim of a container and permit only a straw to access the contents of the beverage container. Still further lids can provide both a spout for drinking and a funnel for adding condiments. Other lids are thin adhesive films that can be applied to the opening of a glass. Still further lids include printing. In short, there are a wide variety of lids.

SUMMARY

In an embodiment of the present invention, an apparatus includes a generally planar portion approximately in a plane. The apparatus also includes a lip portion extending in a direction generally orthogonal to the plane. The generally planar portion is joined to the lip portion at a circumferential edge of the generally planar portion to form a cover for a beverage container. The lip portion comprises a sterilizing agent configured to sterilize a rim portion of the beverage container.

In another embodiment, a method includes forming a generally planar portion approximately in a plane. The method also includes forming a lip portion extending in a direction generally orthogonal to the plane, wherein the generally planar portion is joined to the lip portion at a circumferential edge of the generally planar portion to form a cover for a beverage container. The method additionally includes providing a sterilizing agent configured to sterilize a rim portion of the beverage container, wherein the sterilizing agent is provided in the lip portion.

In a further embodiment, a method includes providing contact information on a disposable cover adapted to cover a beverage container, wherein the contact information is not provided by the manufacturer of the beverage or beverage container. The method also includes receiving contact from a user of the disposable cover. The method further includes coordinating the delivery of a service to the user of the disposable cover responsive to the contact received from the user.

In another embodiment, a cover has the ornamental design substantially as shown in the accompanying drawings, and/or as described in the detailed written description herein.

BRIEF DESCRIPTION OF THE DRAWINGS

For proper understanding of the invention, reference should be made to the accompanying drawings, wherein.

DETAILED DESCRIPTION OF THE PREFERRED EMBODIMENT(S)

Figure 1:
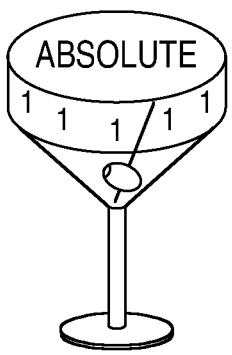
FIG. 1 illustrates various covers according to embodiments of the present invention.
Figure 1:
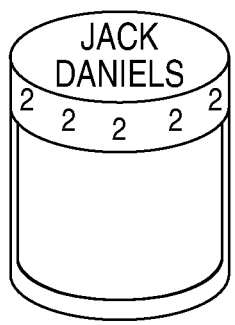
Figure 1:
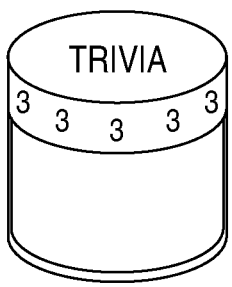
Figure 1:
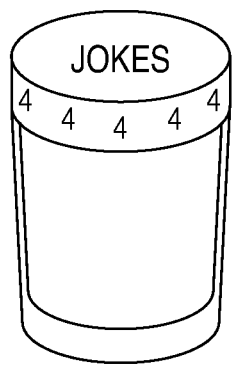
Figure 1:
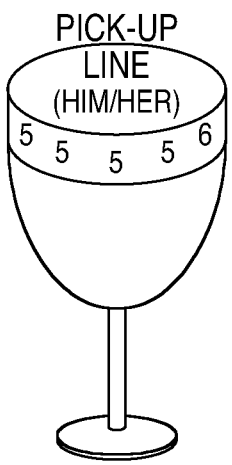
Figure 1:
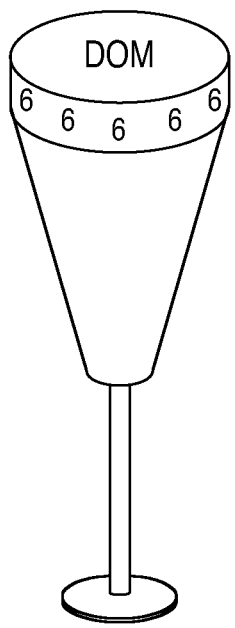
Figure 1:
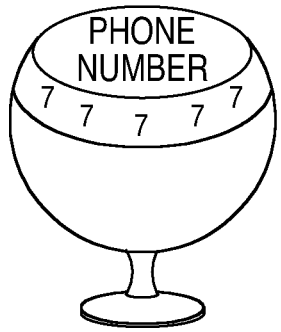
Figure 1:
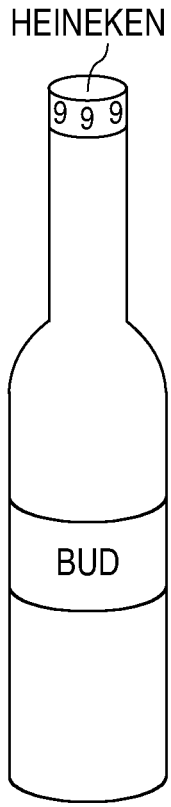
Figure 1:
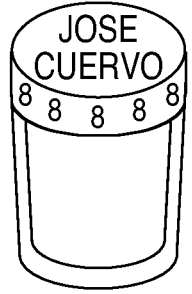

In a restaurant environment, cups can come in a variety of shapes and sizes. Generally, however, in a particular restaurant, cups will all have two common features. Cups will normally appear to be similar to other cups in the restaurant, and cups will have an open top surface, also called the mouth of the cup. In certain instances, users of cups drink from the cup by a straw or similar mechanism. However, in other instances users drink from a cup by placing the cup against their lower lip and tilting the cup to pour the cup's contents into the respective user's mouth.

Cups may also have other features, including sides, a bottom, and optionally one or more handle. Other features, such as a built-in straw, may optionally appear and should not be considered to have been excluded.

The mouth of the cup is normally defined by a rim. Most cups feature circular rims, although other shapes of rims, such as oval, octagonal, hexagonal, or even square are sometimes used. In the examples below, typically a cup with a circular mouth is assumed, but any shape is permitted. Oftentimes, the term "rim" encompasses also a portion of the side of the cup, where the user's lip touches the cup in the ordinary course of drinking from the cup.

A cover can be fitted to the rim and can extend over the mouth of the cup. The cover may be formed in different shapes. However, a cover may have a generally planar section, and optionally a downwardly directed lip portion. The generally planar section can be configured to be concave, convex, domed, or patterned. The patterning can take various forms, such as a bas-relief image or text. High relief and sunken relief images and text are also possible. The lip may similarly be variously decorated. The cover can be decorated with color and/or text. The cover may be configured to use color change materials. For example, the color change may be triggered by time in use or by the temperature of the material in the beverage container.

In many cups, the circumference of the mouth of the cup is larger than the circumference of the base of the cup. In this situation, for example, the cover can be configured to serve two purposes. In a first configuration, the cover may be arranged to cover the mouth of the cup. In a second configuration, the cover may be arranged to serve as a coaster for the base of the cup. Although such a cover can serve two purposes, for consistency of explanation, the "top"

of the cover is a reference herein to the top surface of the cover when it is being used to cover the mouth of a cup, whereas the "bottom" of the cover is a reference herein to the surface of the cover that is facing upward when the cover is in a coaster configuration, that is, the opposite side from the top.

Not all covers may be configured for this dual purpose. For example, some covers may be configured only to serve as covers and not as coasters. In examples where a cover is configured to serve as a coaster, the top of the cover may be patterned with bumps or provided with a high-friction non-slip surface. This non-slip surface may control the behavior of the cover with respect to a substrate, such as a table or bar, on which on the cover is resting when in coaster configuration.

The cover can, in certain instances, be a reversible cover. Thus, the cover may have two sides, each of which can be the "top" depending on how the cover is positioned. Additionally, a lip of the cover, if provided, may be configured to be able to be reversed so that it extends in an opposite direction. To permit such reversal or for other purposes, the lip may be formed of a flexible, resilient material, such as rubber.

In another embodiment, the cover can originally be manufactured in a flattened configuration, with the lip extending circumferentially. In such an embodiment, a thin layer of metal can be embedded within the lip and optionally within a portion of the generally planar section. This metal may permit the lip to be bent into a particular shape and then to maintain that shape.

The lip can also be configured to be a snap cover, that is configured to expand over the rim of a cup with pressure and snap into place due to its own resilience. Thus, in certain embodiments, the lid may be applied to a disposable cup, such as a paper, Styrofoam, or cardboard coffee cup.

The cover can be a removable cover or a permanent cover. In the case of a removable cover, the cover can be either secured or unsecured. An example of an unsecured cover is a cover that generally rests on the mouth of the cup and is held in place by gravity.

A secured cover may interface with the rim or some other portion of the cup. For example, the cover can interface with a portion of a handle or other protrusion of the cup. Alternatively, the cover may interface with a portion of the side of the cup slightly below the rim. However, in general this area may be referred to as the rim in a broad sense.

In some cases, a secured cover can be configured with a locking mechanism that prevents unauthorized removal of the cover. For example, the cover can be configured to tightly grip the cup in a secured setting and relax or release that grip in an insecure setting. The setting can be controlled by entry of personal identification number (PIN) that can be supplied to a top or side surface of the cover. Alternatively, a biometric interface can be provided, such as a fingerprint scanner or retinal scanner.

There are various ways that the cover can interface with the rim. For example, the cover can form a simple interference fit by simply being tightly fitted to the outside surface of the rim. Alternatively, the cover can incorporate a clipping mechanism to enhance the simple interference fit. The interference fit can be enhanced by a mechanism that permits the tightness of the fit to the outside surface of the rim to be dynamically altered.

There are various configurations that may permit such dynamic alternation. For example, a cam can be supplied in a circumferentially outer portion of the cover, so as to lie between a flexible interior circumference that is configured to touch the outside of the rim of the cup and a rigid outer circumference of the cover, opposite the interior circumference. In a first position, the cam can present a narrow diameter to the outside surface of the rim, providing a loose fit. In a second position, the cam can present a wide diameter to the outside surface of the rim, providing a tight fit. Other mechanisms for tightening or loosening the cover are also permitted.

Additionally, it is possible for the cover to be screwed onto the rim. This may require that the rim be threaded, either in whole or in part. Other kinds of fits are also possible. For example, the rim may include a protrusion in a circumferential direction, and the cover may be configured to snap over the protrusion.

Furthermore, the cover may include a contact adhesive or some other chemical adhesive agent that permits the cover to bond to the rim, or a portion of the rim, of the cup. This adhesive may be a non-permanent low tack adhesive.

Instead of, or in addition to, the low tack adhesive, an inside surface the lip of the cover may be provided with a sterilizing agent. The sterilizing agent may be a weak sterilizing agent, such as lemon juice or similar weak acid solution, or the sterilizing agent may be a stronger sterilizing agent such as high concentration alcohol. Other sterilizing agents, such as a silver solution, are also permitted.

In cases where the cover is to be removed and normally drinking to be performed on the cup, a sterilizing agent may be selected to be a sterilizing agent that is not poisonous. An example of a poisonous sterilizing agent would be bleach.

Another alternative for sterilization is to provide ultraviolet light through the interior surface of the lip of the cover. The ultraviolet light could be generated in the generally planar section and then transmitted by a light guide, such as optical fibers or mirrors, to the edge. Thus, in certain embodiments there can be sterilization of a portion of the cup or bottle that is typically contacted by a user's lips and/or tongue. The ultraviolet light can also or alternatively be used to purify the contents of the cup. For example, the ultraviolet light can be supplied downward from a central portion of the generally planar portion of the cover. Also, or alternatively, the ultraviolet light can be used to self-clean the cover and/or the cup, after the contents are removed.

Alternatively, an arm can extend downward from the central portion of the cover and can be configured to be submerged in the contents of the cup. The arm can supply the ultraviolet light to the contents of the cup. Alternatively, or in addition, the aim can provide other functionality. For example, the arm can test for the presence of undesired chemicals, such as Gamma-hydroxybutyrate (GHB) or scopolamine. The arm can also supply desired chemicals.

The aim can be configured to be rigid or flexible. In some cases, the arm can be extendable or retractable. For example, the arm can hinge downward from a generally planar portion of the cover. The arm can include one or more elbows that are configured to permit multiple foldings/unfoldings of the arm over a range of movement.

The arm can also be configured to perform other tasks. For example, the arm or another component can be configured to analyze the content or makeup of, or to determine the ingredient(s) of drink or beverage. The system can be configured to display results of the analysis on a planar portion thereof.

Furthermore, in certain instances the arm or another device, such as a retractable tube, can be configured to probe the contents of the cup. The arm, tube, or the like can draw a sample of the contents of the cup into a reservoir in the cover. The amount of contents in the reservoir may vary.

Thus, for example, in certain embodiments a small amount, such as single drop of the liquid can be transported into a reservoir, which can be a small void, divot, hole, or the like. The transport mechanism to bring the liquid to the reservoir can rely on wicking in certain embodiments. In other embodiments, the liquid can be wicked up into a string or paper element, and the string or paper element can then be mechanically drawn into the cover for analysis.

After analysis, however performed, the results can be displayed to a user of the cover, or can be communicated wirelessly to a remote user or remote data center. The results can be displayed electronically or chemically. For example, a color-change reaction can be used to indicate the results in certain embodiments. In other embodiments, the results can be displayed as text on a user interface of the device. The user interface can be on the top of the device or around an edge of the device. In certain embodiments, there can also or alternatively be a user interface on the underside of the device.

In certain embodiments, the analysis tool can be configured to receive a sample other than from the contents of the cup. For example, the analysis tool in the cover may be configured to receive a sample of saliva. The tool can then be configured to configured to analyze the sample for diseases, such as contagious diseases. As in the previous cases, the results of such analysis can be displayed.

A further analysis tool may be installed in the cover and configured to test breath or atmosphere. The tool may be configured to alert the user of an excessive amount of carbon monoxide or other dangerous gas. Alternatively, the tool may be configured to sample the breath of a user and determine whether the user is healthy. For example, the device may be configured to determine whether the user has a disease or is intoxicated. Thus, in certain embodiments, the device may include a breath analysis sensor to determine approximate blood alcohol content.

Other ways of securing the device to a beverage container also permitted. For example, a pump mechanism can be provided. The pump mechanism can be configured to create negative pressure or suction between the device and the beverage container. Thus, external atmospheric pressure can be used to secure the lid to a glass or bottle.

Various electrical components and systems can be provided. For example, a location system can be included. The location system can utilize a global positioning system (GPS) or other triangulation or multilateration technology. The system can be configured to identify a particular location within a place of business, such as a particular bar stool, table, or service area of a restaurant. The system can also include a barometer or other altitude measuring device that can identify a particular floor on which the system is located. The system can be equipped to communicate its location, either as a position, or using a beacon or homing signal. Another device can be used to locate the position of the system. The other device can indicate to its user the position or direction of the system. Thus, for example, a waiter or waitress can be provided with the other device and can locate a particular patron using the system.

The system can also be equipped with various sensors or devices configured to be read by sensors, such as a radio frequency identification (RFID) tag. The RFID tag can permit location of the system and can also provide additional information, such as a serial number of the cover.

The system can also be equipped to locate other similar peer devices within an establishment. For example, each system can send out beacon information about the system and/or the user, and this information can be broadcast to all other nearby systems. In alternative embodiments, the system can send out information that can be disseminated over a metropolitan area, a regional area, a national area, or worldwide.

The information can provide user-provided information about the user, such as the likes/dislikes of the user, taste in beverages of the user, age and sex of the user, and so on. For example, the information can include a profile of data about the user, such as can be provided on a social media or dating website. The system can be provided with a camera that can take a picture or video of the user or the user's drink, food, or other object of interest.

The system can be provided with a variety of user interface options. For example, the system can be provided with audio and visual outputs. The system can, in certain embodiments, be provided with Bluetooth or other wireless communication technology. Thus, for example, the system can be configured to operate in connection with a wireless headset. The wireless headset can provide audio to the user and can also provide a microphone for receiving audio from the user.

Other user interface options are also permitted. For example, the system can be configured to provide a three-dimensional holographic projection. In certain embodiments, for example, the system can include three vertical walls, and the system can be configured to provide a holographic illusion visible from a fourth side. In other embodiments, the system may use lasers or focused light to provide a display projected above a generally planar section of the lid. The system can be provided with a particle source, such as a smoke source, that can make light projected from the system more visible immediately above the system.

In certain embodiments, a hologram digital waiter or waitress can take drink or food orders. The system can either project an image of a live but remote person or can project an image of a virtual person. The system can include a listening device configured with speech recognition to interpret orders, or can transmit the speech signal to a remote person.

In certain embodiments, the system can be provided with a variety of mechanisms for alerting the user of the system, the owner of the system, or others. The alerts can be audio alerts, such as alarm bells, ringing noises, sirens, whistles, or the like. Alternatively, or in addition, the alerts can be visual alerts, such flashing or blinking lights or changes of color of lights of a device. Alternatively, a display can provide alerts as text or images.

The system can also include a variety of security mechanisms. For example, the system can include a combination or keyed lock. The combination or key mechanism can be a physical mechanism or can be a virtual mechanism on a top surface of edge of the system. The mechanism can require the user to input a code to enable or disable the security system. Alternatively, the system can use biometric data, such as a fingerprint, retina scan, or DNA test to verify the identity of a user and secure the system.

For example, before a user goes to a restroom from a table, the user can place the system on top of a beverage glass and activate a security system. If the system is moved in an unauthorized way in the user's absence, the user can be alerted. When the user returns, the user can deactivate the security system by entering a code, fingerprint, voiceprint, or password. The password can be a spoken or written password.

As noted above, the system can include a camera or video camera. The system can include a pair of camera lenses offset to provide three dimensional images. The system can also include a camera configured to provide a half-spherical image from the top of the generally planar section of the device.

The device can include a variety of advertising and other display mechanisms. For example, the top and bottom surfaces of the device can be provided with static, semi-static, or dynamic images. Likewise, an edge surface of the device can be provided with a curved display that can permit an advertisement to be displayed around the circumference of a glass, when the device is placed on top of the glass. The brim of the lid can also, or alternatively, be provided with a window pocket that can permit an advertisement to be inserted and removed, thereby providing a semi-static display of information.

In certain embodiments, the system can be configured to permit commercial transactions. For example, the system can be provided with a credit card reader, including a magnetic strip reader, chip reader, and/or the like. The system can also be provided with preconfigured buttons that permit ordering of drinks or other items from a preset menu.

The system can further include a web browser. The system can include communications hardware configured to permit the system to allow a user to user the Internet. The Internet can be used for the commercial transactions mentioned above, as well as for other purposes.

Certain embodiments can include capabilities of displaying television and/or videos. For example, certain embodiments can include a television tuner and can be configured to permit the watching of broadcast television. Also, or in addition, video data can be streamed over an Internet connection of the device, for example in connection with a web browser, application, or program, such as a video chat program. The device can also or alternatively be configured to include a computer readable memory. For example, the system can include random access memory (RAM). The memory can be loaded with video stored in a computer-readable format, such as an mp4 recording.

As mentioned above, the system can be used to provide advertisements. The advertisements can be third party paid advertisements or can be advertisements of menu items, drinks, or the likes of the owner of an establishment in which the system is provided.

The system can also be configured to permit a variety of recreational activities. For example, a user interface can be configured to permit gambling, such as poker, pachinko, or keno. Other gambling, such as slots, video poker, video blackjack, roulette, and so on are also permitted. The system can be configured to operate in connection with a state lottery.

In certain embodiments, the system can be configured to play games with the user. For example, the system can be configured to quiz the user regarding sports trivia. Also, or alternatively, the system can be configured to play other games, such as Sudoku, chess, checkers, Monopoly, or the like. The system can be configured to play one-player games, multi-player games in which the system is passed from player to player, or multi-player games over a communication link with another system.

The system can also be used in connection with a taxi service. For example, the system can be configured to permit the user to obtain taxi service upon request.

As mentioned above, the system can include a device for reading credit cards, debit cards, or gift cards. The system can be configured to permit a user to use the system to pay for a restaurant or bar tab, to pay for a cab, or the like, using a credit or debit card.

The system can also be configured to communicate with a disk jockey (DJ) or jukebox. The system can be configured to permit a user to make a request for a particular song or category of song or other music. For example, the system can display a list of available songs as a menu, and can permit the user to request a song from the menu. The system can also permit the user to pay to have the request given priority treatment.

The system can also be configured to permit communication between other peer systems. For example, a lid according to certain embodiments can be configured to permit a given bar patron to communicate with other patrons at the same bar. Although a bar is provided as an example of a place where the system could be deployed, the system can also or additionally be deployed in other venues, such as at coffee houses, casinos, or the like.

Certain embodiments can be used as a lid for various containers. For example, certain embodiments can be used in connection with reusable glasses that are mainly rested on tables, bars, card tables, pool tables, and the like.

Certain embodiments may be reusable lids that can be washed or otherwise sterilized between uses. Other embodiments, however, may be disposable lids. Disposable lids may be made of an inexpensive material, such as cardboard, and may include a minimum of electronic components. The disposable lid may be configured to display an advertisement, temperature information, or the like, for a short time.

In certain embodiments, electronic components, such as a processor, controller, or microchip may be embedded in the cover. The components may be incorporated together with a power storage device, such as a battery. Additionally, the components may be provided with a power replenishment device, such as a wireless charging interface.

Certain embodiments may provide various musical interactions. For example, certain embodiments may provide audio output, such as music. The system can also, or alternatively, include an interface configured to permit the user to play music using the system as an instrument, optionally via an application installed on the system.

The system can also be configured to accept music requests. The music requests can be transmitted to a jukebox system or to a live band. The system can also be configured to permit the device itself to download music. Thus, in certain embodiments, the music request can be a request to download music from a remote server.

Certain embodiments can be provided with navigational aids, such as maps. The maps can be static or dynamic. For example, if it is detected that a user is on a first floor of a restaurant, the maps displayed can be maps of the first floor. Also, or alternatively, the map can be configured to show an area immediately surrounding a current location of the system.

The maps of the system can display various points of interest, such as the location of any active places, where service is provided, or restrooms.

As mentioned above, a lid according to certain embodiments can be configured to communicate with other similar lids. These lids can be used by patrons of an establishment to communicate with one another. For example, the device can be used to text other users as a way of breaking the ice or otherwise beginning or continuing a conversation. The system can electronically display jokes, trivia, or the like, to assist users in the communication process, or simply to amuse or instruct the user of the system.

Certain embodiments of the system or device can include various sensors. For example, the system can include a barometer, thermometer, hygrometer, or the like. The system can also include motion sensors, configured to detect motion of the system, either in general or with respect to a beverage container. The system can also include other sensors, such as pressure sensors.

Other accessories can be provided with the system. For example, the system can be provided with a toothpick dispenser configured to dispense or one more toothpick to the user of the system.

Another accessory that can be included can be a breath analysis machine, such as a breathalyzer. Additionally, or alternatively, other mechanisms for determining blood alcohol content can be provided. The mechanism can be configured to trigger an application that can summon a taxi.

In certain embodiments, the system is configured to be remotely controlled or to remotely control another device. For example, the system of a bar patron can be remotely controlled by a bartender to provide information regarding drinks, solicit new drink orders, or the like.

The system can also be configured to control a temperature of a beverage in a container. For example, the system can be configured to have good insulation properties, thereby permitting hot contents to remain hot and cold contents to remain cold. Alternatively, or in addition, the system can be provided with mechanisms for actively heating or cooling a beverage. For example, the system can be configured to perform an exothermic or endothermic reaction to produce or absorb heat from the beverage. Also, or in addition, the system can be provided with a heating coil configured to warm the contents of—for example—a coffee cup.

As mentioned above, certain embodiments can have various security mechanisms. The security mechanisms can include voiceprint analysis or other voice recognition mechanisms. The security can prevent an unauthorized user from using the system to order drinks on behalf of the user, without the user's knowledge.

Certain embodiments may also include voice analysis tools. These voice analysis tools may convert input speech into phonemes or otherwise analyze the input speech. Additionally, in certain embodiments, the tools may be configured to provide a translation from a first spoken language to a second spoken language. In certain embodiments, the translation can be performed on a text input.

Certain embodiments can also include a vibration mechanism. The system can include a motor or other mechanism that is configured to produce a mechanical movement of the system. Also, or in addition, the system can include a sonic system that is configured to produce sound energy. For example, an ultrasonic component can be configured to direct sound energy into a beverage container. The sound or other vibration can be configured to stimulate the contents of a beverage container. Thus, certain embodiments may be configured to add air to wine and/or mix contents of a beverage glass or disposable cup The generally planar section and/or the lip portion of the cover may be formed of a single material, such as molded resin, or it may be formed from a composite of materials in various layers. For example, a decorative layer may be formed on the top surface of the cover, whereas a water-resistant layer may be formed on a bottom surface of the cover. The water-resistant layer may be a wax layer.

The cover may include an insert. The insert may be removably inserted into a pocket or the insert may be permanently embedded or laminated into the cover. The insert may be decorative or informative. For example, the insert may provide advertising information or instructions.

Alternatively, the insert may have a functional purpose. For example, the insert may be designed to heat or cool the rim of the cup. Thus, for example, the insert may be a chemical insert configured to perform an exothermic or endothermic reaction to either heat or cool the rim of the cup. In such a situation, the inside lip of the cup may be formed of a material with good thermal conductivity, such as a metal.

The insert can be configured to provide the portion of the device that may contact the rim or contents of the cup. Thus, the insert may permit quick reuse of the cover. For example, the insert may be replaced with a new insert rather than needing to wash/sterilize the entire cover.

In certain embodiments, the insert may be paper or cardboard. In other embodiments, the insert may be made from a transparent material or a material that is close to transparent with respect to ultraviolet light. In such cases, an ultraviolet light source can be arranged above the insert and configured to shine on the contents of the cup, while being protected from contact with the contents of the cup by the insert.

Alternatively, the insert can be configured to be displayed through a window on the top surface of the cover. Thus, the insert can be configured to provide advertisement or other information.

The cover can also include a reservoir. This reservoir can include a sample of the contents of the cup for testing. The testing may including testing for diseases, such as diseases that may be spread by the use of the cup. The reservoir can also have additional purposes or uses.

In certain embodiments, the cover may be equipped with an electronic display. The electronic display may be operated by battery power, by a photodiode, or other power supply means. Thus, the device may be solar powered or may be powered by thermal energy, drawing from the heat of the contents of the beverage container. The electronic display may be always on, or may be triggered by pressure or acceleration sensors in the cover.

Thus, for example, the cover may configured to display a message when the cover is placed onto a cup, but the cover may be configured to be off when not placed on a cup. Thus, battery life of the cover may be conserved.

For determining a duration of time that the cover is in use, the cover may be equipped with a timer. The timer may also be connected to the display to show an indication of how long the cover has been used, or the time of day, or the time until a restaurant or bar associated with the cover closes or stops serving alcoholic drinks.

The cover can be configured to have an interactive display. Thus, the cover may further include a user interface. The user interface may include one or more button or toggle, or alternatively may include a touch-sensitive surface. The cover may also be configured to interact with the user through the use of one or more accelerometer.

The interactive cover may be configured to permit the playing of individual games or cooperative or competitive games. In certain embodiments, the interactive cover may be configured to permit communication with other similar interactive covers in a local area—such as a particular restaurant—or a wide area, such as across a country.

The cover can also be equipped with a temperature-sensing device. This device can be a temperature-sensitive pigment that changes colors depending on the temperature of the environment, or the device can be a thermometer. The cover can be configured to display temperature information regarding the cup or its contents to the user.

The cover can be equipped with a speaker or similar audio device. The speaker can be configured to inform the user of various information or the speaker can serve as an alarm. For example, the speaker can be configured together with an accelerometer or pressure sensor to provide an audible alert when the cover is lifted from the cup. Additionally, the alert can include a warning such as, "be careful, your drink is still hot," so as to alert the user that the drink may not yet be at a maximally safe temperature.

The cover can also be equipped with a communication device that permits the cover to communicate with another device. For example, the cover may be able to communicate with the device of a bar-tender to indicate on the cover of the device or by use of audio means a current amount of a bar tab or a number of drinks served to the user of the cover. The cover may also be configured to provide an audio or visual alert to the user of the cover, or to the bartender, when a predetermined condition (such as a service limit on drinks or a spending limit set by the user) has been met.

In further embodiments, advertisements may be displayed on the cover of the cup, either statically or dynamically. A static advertisement may be achieved by, for example, placing an advertising insert in a pocket of the cover, embedding the advertising in molded resin, or laminating the advertising onto the top surface of the cover.

A dynamic advertisement may be an advertisement that is configured based on a number of drinks consumed, duration of time that the cover is in use, or the like. Thus, for example, the dynamic advertisement may initially invite the user to order additional drinks, but subsequently may advertise the services of a taxicab company or the like. Additionally, the cover may be configured to take into account the time of day, and suggest the purchase of traditional morning drinks, such as coffee or orange juice in the morning, soft drinks and iced tea around lunch time, and wine, beer, cocktails, and other alcoholic drinks in the evening.

Moreover, the dynamic advertisement may begin to advertise other products from a point of sale establishment, such as a coffee shop. Subsequently, however, the cover may begin to display other advertisements, such as options for lunch or dinner, as time progresses. The advertisements may take into account the geographic location of the device or of the place where the device was sold.

Additionally, the cover may be configured to display the user's name in a prominent way, so that multiple covered cups can be easily distinguished from one another. This can be accomplished by the use of an interactive programmable display on the cover, and the name may be entered by the user of the cover or by a bartender operating a remote display control device. The name may alternatively be displayed by having the name written on a top surface of the cover.

The name or other information about the user may be able to entered electronically and displayed by a programmable display on a surface of the cover. The same display may also display the contents of the beverage container. This may avoid the need for a barista to announce the name and contents of a given beverage container, or may enable the barista to make such an announcement with higher accuracy, even if the cup is passed through many stages of preparation. For this purpose, or other purposes, the cover and/or the beverage container itself may incorporate a scannable microchip.

For having the name written on the top surface of the cover, the top surface can be configured to have an erasable re-writable surface, like a chalkboard or a dry-erase board. Alternatively, the cover can have a paper layer as a top layer of the cover, and the writing can be performed on this paper layer. This approach may be suitable when the cover is a disposable cover.

In a further alternative, the cover may be adapted to permit the application of either a permanent or removable label. Then, a label with the user's name may be adhered to the top surface of the cover.

Similarly, the advertising can be accomplished by providing a label on the top surface of the cover. For example, in a restaurant environment, the label can indicate a special of the day or a daily menu.

The cover can also be used for communication from the user to restaurant staff or a bartender. For example, the user can write on the top surface of the cover. Alternatively, in the case of a reversible cover, one side of the cover can indicate that continued service is desired with a message such as, "Keep the drinks coming," and the opposite site of the cover can indicate that the user is finished, with a message such as, "Check please!"

The cover can also be integrated into a dispatching system. For example, a dispatching system can include at least a call receiving center and a dispatch center, which may be the same center. The call receiving center can be configured to receive calls from customers who have received an advertising message from a cover according to certain embodiments of the present invention.

The dispatching center may then dispatch a service provider to attend to the needs of the customer. For example, the service to be provided may be a taxicab service. Alternatively, other services, such as a bail bondsman services, escort services, or security services may be the services to be provided.

The dispatching center may contact a local cabbie directly or may contact the dispatcher of a local taxicab company and coordinate pickup of the customer with the local taxicab company. Alternatively, the dispatching center may transfer a call from the user of the cover to the dispatcher of a local taxicab company.

In another embodiment, the user sends an email, short message service (SMS) message, or text message to the dispatching center, and the dispatching center provides the phone number for a local taxicab company, or provides the number of the user to a local taxicab company.

In specific embodiments, a cover or lid can be designed for specific or standard-sized cocktail, wine, martini, lowball, high-ball, margarita, beer stein, pint, champagne, cognac, port, shot, hurricane, Armagnac, dessert wines, grappa, and scotch glasses, and the like, including also glasses that are for consumption of non-alcoholic beverages.

Additionally, a separate and specific lid design can be used for a beer bottle or the bottle of a non-alcoholic bottled drink, such as root beer. The lids can be designed to cover the glass or bottle when the owner of the glass or battle is absent, distracted, or concerned about the security of their drinking vessel.

The design of the lid, according to a particular embodiment, can include a numbering system and can be color-coded to allow the owner's drinking vessel to be identified. The numbering system may be, for example, covers each having a single number from 1 to 1000. The color coding scheme may be blue for men and pink for women. Additionally, the lid can designate that a location is occupied, and can allow service providers, such as waiters and bartenders, to locate a corresponding patron.

The lids can be designed with specific logos, jokes, trivia, wedding details, upcoming events, pick-up lines, local taxicab numbers, a responsible drinking designation, or any combination of those. The logos can include locals of hotel chains, beverage manufactures, restaurants, casinos, sports teams, or the like.

The lid can be made from a green-based or recyclable material, such as recycled paper or corn. The design may include a natural antiseptic inner coating, such as a coating derived from a lemon. This may help to protect the lip area of the vessel from germs and may promote overall hygiene.

FIG. 1 illustrates several embodiments of the present invention. As shown in FIG. 1, covers can be designed for a variety of glasses and bottles. A martini glass cover may be equipped with a via that permits a straw, toothpick, or stirrer to remain in the glass despite the presence of the cover. As shown, the lip of the cover may be provided with multiple representations of a unique number, in this instance the number is 1. Additionally, the manufacturer of a vodka may be advertised on the top surface of the cover.

The cover of a high ball glass may be similarly constructed, although there may be no requirement for a via for a straw or the like to pass through the cover. The cover may be colored, and the manufacturer of a whisky may be advertised on the top surface of the cover. The number 2 is provided repeatedly around the lip of the low ball glass.

The cover of a low ball glass is also illustrated. In this instance, the cover of the glass displays trivia. The trivia may, for example, be a geographic question, such as "What is the tallest mountain in the U.S.?" The reverse side of the cover may have the answer printed, or the answer may be printed upside down in a much smaller font on the cover. This cover has the number 3 repeatedly printed on the lip of the cover.

A pint glass cover, as illustrated, may include a joke written on the top surface of the cover. The number 4 is shown as repeatedly printed on the lip of the cover.

A wine glass cover is shown with the number 5 repeatedly printed on the cover. On the top surface of the wine glass cover, a pick-up line has been printed. The pick-up line can be customized to be a pick-up line for picking up a particular sex, either male or female. The cover can also be colored so as to make easy identification of an appropriate pick-up line easier. For example, pink covers may indicate pick-up lines to be used by women, and blue covers may indicate pick-up lines to be used by men. The lip of the cover may be decorated with the number 5.

A Champagne glass cover may have the number 6 on its lip. The top surface of the cover may advertise a premium Champagne.

A cognac glass cover may have the number 7 printed on its lip. The top surface of the cover may have a phone number printed. This phone number may be the phone number of a local taxicab company or a nationwide taxicab dispatch center. Other phone numbers, such as the phone number of the restaurant that is providing the covers, are also possible.

A shot glass may have the number 8 printed on its lip. The top surface of the cover may advertise a tequila manufacturer. Likewise, a beer bottle cover may advertise the manufacturer of a beer. The beer bottle cover shown may have the number 9 on its lip.

In the examples above, there is no requirement that the manufacturer of the beverages advertised corresponds to the actual beverage in the container. However, the advertisement may be tailored according to the kind of beverage. For example, an imported beer manufacturer may be advertised, even if the cover is going on a domestic bottle of beer.

The numbered lips have been shown with a variety of numbers, and a different number for each kind of beverage holder. However, there is no requirement that numbers be assigned in this manner Thus, for example, shot glass covers may come in a variety of different numbers, from 1 to 100, and not only the number 8.

Figure 2:
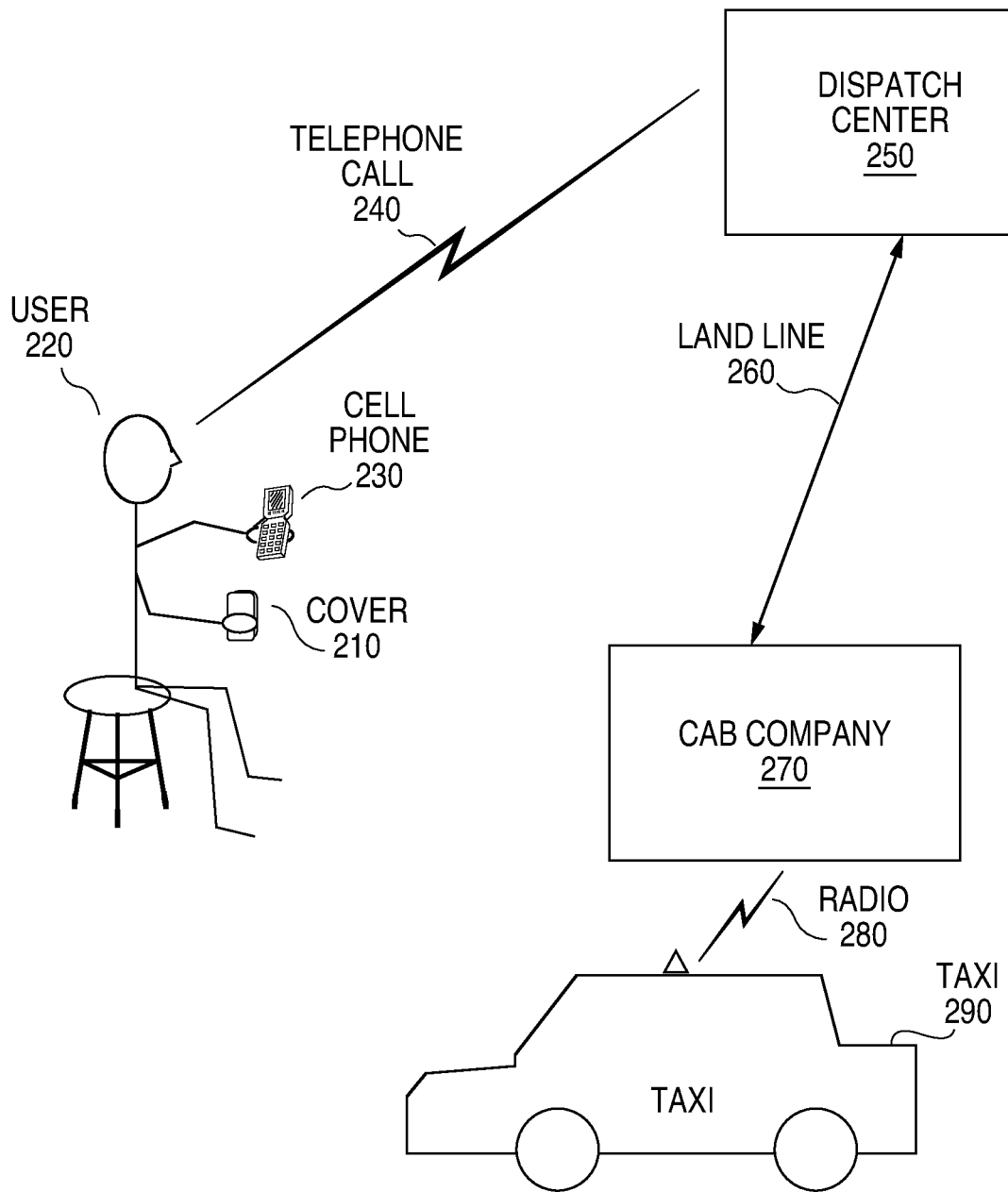
FIG. 2 illustrates a system according to certain embodiments of the present invention.

FIG. 2 illustrates a system according to certain embodiments of the present invention. As shown in FIG. 2, a cover 210 may advertise the phone number of a central dispatch for taxis. The user 220 may employ a cell phone 230 to make a telephone call 240 to the dispatch center. The dispatch center 250 may obtain the geographic information of the user 220 and determine the location of the user 220, as well as the urgency of the need for transportation by the user 220.

The user 220 may be one or more people. The user 220 need not make the call personally: someone could call on behalf of the user. Instead of cell phone 230, another communication device, such as a text messaging device, an emailing device, or a conventional land-line phone can be used. The dispatch center 250 can obtain the geographic information by requesting it from the user 220 or person calling on behalf of the user. Alternatively, the dispatch center 250 could use caller ID or a geographic tag provided by the communication device of the user 220 to determine a location.

The dispatch center 250 may then use a land line 260 to call a local cab company 270 and determine the availability of transportation, or forward the user 220 to the local cab company 270. The local cab company 270 may then radio 280 to a taxi 290 of a fleet of taxis (not shown) and direct the taxi 290 to pick up the user 220.

Instead of using a land line 260, the dispatch center 250, could contact the local cab company 270 according to other communication methods. For example, the dispatch center 250 could call using a Voice over Internet Protocol (VoIP) phone or could use a text messaging or e-mail system. Likewise, the local cab company 270 could contact the taxi 290 by the use of a mobile phone or pager, rather than by use of radio 280.

In certain embodiments, the user 220 may then present the cover 210 to the drive of the taxi 290 to serve as a voucher or coupon for payment or subsidy of a ride home.

Figure 3:
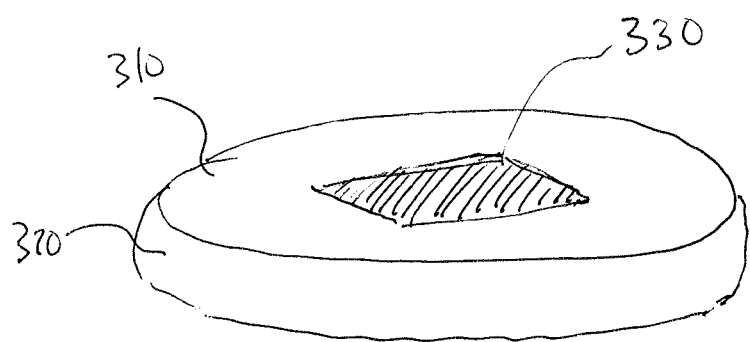
FIG. 3 illustrates an apparatus according to certain embodiments.

FIG. 3 illustrates an apparatus according to certain embodiments. As shown in FIG. 3, an apparatus can include a generally planar portion 310 approximately in a plane. The apparatus can also include a lip portion 320 extending in a direction generally orthogonal to the plane.

The generally planar portion 310 can joined to the lip portion 320 at a circumferential edge of the generally planar portion to form a cover for a beverage container. The apparatus can include a variety of hardware embedded therein or thereon. For example, the apparatus can include a user interface 330, which may include a touchscreen.

In certain embodiments, the generally planar portion can include at least one microchip including memory embedded therein. The at least one microchip and memory can be configured to control a user interface on a top surface of the generally planar portion. The at least one microchip and memory are configured to display information regarding contents of the beverage container based on at least one of data input externally or a sensor reading.

Figure 4:
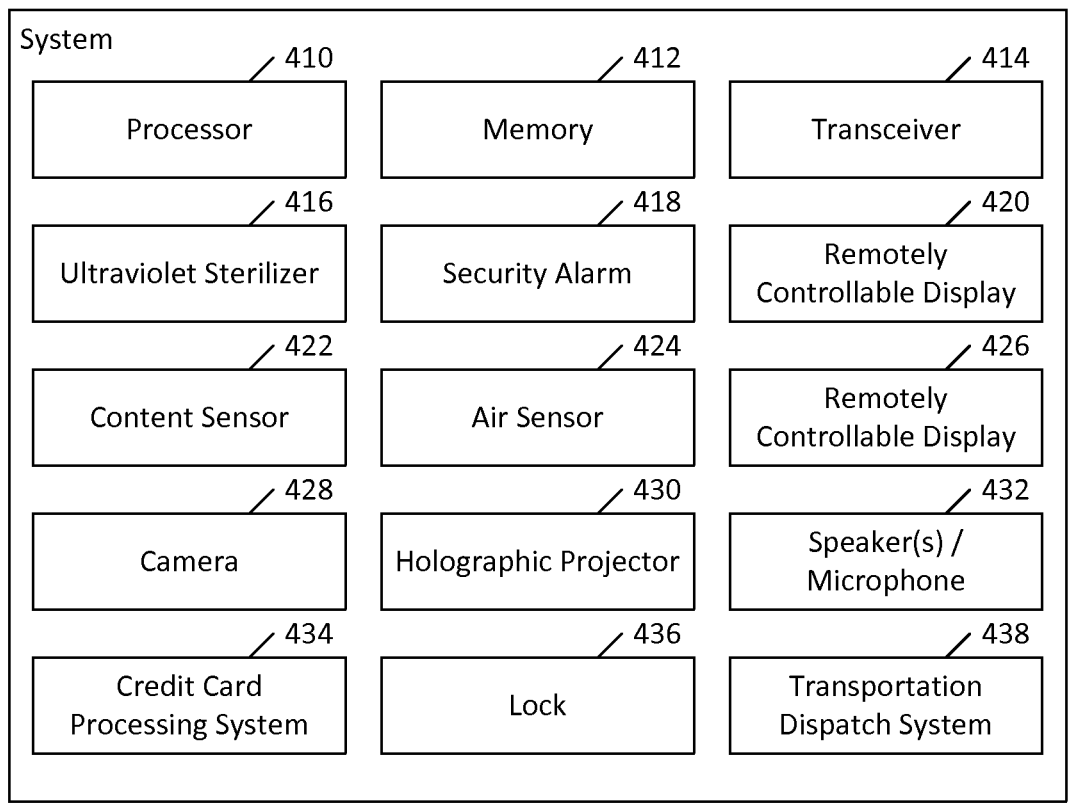
FIG. 4 illustrates a system block diagram of certain embodiments.

The apparatus can also include a variety of systems and components. FIG. 4 illustrates a system block diagram of certain embodiments. As shown in FIG. 4, the system can include at least one processor 410 and at least one memory 412. The processor 410 may be a microprocessor, an application specific integrated circuit, or other controller or processing circuitry. The at least one memory 412 may be any form of computer storage, such as a random access memory (RAM) or field programmable gate array (FPGA). The at least one processor 410 and the at least one memory 412 may be configured to store and process data and to perform a variety of functions, either alone, or in combination with other hardware or software.

The system can also include at least one transceiver 414. The at least one transceiver 414 can be any form of communication hardware. For example, the at least one transceiver 414 can be configured to communicate over a wireless local area network or using Bluetooth. Other communication protocols, such as cellular or infrared communication protocols, are also permitted.

The system can also include an ultraviolet sterilizer 416 configured to sterilize using ultraviolet light. The sterilizer 416 may include an ultraviolet light source and guides, reflectors, concentrators, or diffusers, configured to project the light onto a target surface. The sterilizer 416 can be configured to project light from, for example, the bottom or lip area of the system. In certain embodiments, the sterilizer 416 can include a transparent layer on a bottom surface of the system disposed below the ultraviolet light source and configured to permit ultraviolet sterilization of the beverage container or contents of the beverage container. In certain embodiments, the ultraviolet sterilizer 416 can be configured to sterilize a rim area of the beverage container. In other embodiments, the ultraviolet sterilizer 416 can be configured to sterilize the inside of the beverage container or the contents of the beverage container.

The system can also include a security alarm 418 configured to detect removal of the system from the beverage container. The security alarm 418 can be equipped to provide audio, visual, and/or vibrational alarms when a predetermined condition is met. The predetermined condition can be a tampering condition, indicating that it appears someone has attempted to unlock the system without authorization or a movement condition, indicating that it appears someone has removed the system from the beverage container. Additionally, or alternatively, the security alarm 418 can send a message to a remote application server and/or can send a short message service (SMS) message to a user of the system. Other means of remote or local communication are permitted. Also, other conditions besides the above-listed conditions can be configured. For example, the security alarm 418 can be configured to detect removal of the system from a bar area or from other geographic coordinates or local proximity.

The system can further include a remotely controllably display 420 disposed on a side of the apparatus opposite the beverage container. Alternatively, or in addition, the display 420 can be on the lip area of the system, facing away from the beverage container. The display 420 can be a liquid crystal display (LCD) or an organic electroluminescent display (OELD), among other options. The display 420 can be remotely controllable via the transceiver 414.

The display 420 can be configured to display various information. For example, the remotely controllable display 420 can be configured to receive and display a user name and contents of the beverage container.

The system can also include at least one content sensor 422 configured to detect the presence of an undesired substance in the beverage container. The sensor 422 can configured to display a sensing result on the remote controllable display 420. The sensor 422 can rely on a variety of techniques, including the liquid sampling techniques described above.

The system can further include at least one air sensor 424 configured to analyze the breath of a user of the apparatus to determine a blood alcohol concentration. Also, or alternatively, the at least one air sensor 424 can be configured to test the atmosphere for unwanted substances, such as Carbon Monoxide.

The system can also include at least one location sensor 426 configured to detect a position of the apparatus and to communicate the position of the device to a remote device.

The system can also include a camera 428 mounted to a top surface of the system and configured to take a panoramic or semi-spherical picture and to communicate the picture remotely, for example using the transceiver 414. The camera 428 can also or alternatively be configured to tag the picture with a description of a food or drink order, in addition to other tags, such location of the picture and time of day of the picture.

The system can also include a holographic projector 430 system configured to project an image of waiter or waitress, provide audio associated with taking a drink or food order, and communicate responses by the user to a remote device. The communication of audio can be provided via speaker(s) 432. The speaker(s) 432 can provide mono or stereo audio. The speakers(s) 432 can optionally also include a microphone.

The system can further include a credit card processing system 434 configured to process payment for the contents of the beverage container. The credit card processing system 434 may rely on the transceiver 414 to communicate with a remote server to determine whether charges to, or withdrawals from, a credit card, debit card, or gift card are authorized.

The system can also include a lock 436 configured to releasably secure the system to the beverage container. As described above, such a lock 436 can be variously configured, such as utilizing mechanical and/or electrical systems and relying on PIN information or biometrics, among other options.

The system can further include a transportation dispatch system 438 configured to request a ride for a user of the apparatus from a cab company or ride sharing program. In certain embodiments the transportation dispatch system 438 may include the capability of performing a call to a cab company or the like, for example using voice over internet protocol (VoIP) and relying on the transceiver 414 connected to an Internet connection.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

What is claimed is:
1. An apparatus, comprising:
a lid comprising at least one sensor integral to the lid;
a lip portion extending in a direction orthogonal to the lid, wherein the lid is joined to the lip portion at a circumferential edge of the lid to form a cover for a beverage container, and
wherein the lid comprises at least one user interface; and
an arm extending in a direction orthogonal to the lid from a central portion of the lid and configured to supply ultraviolet light to contents of the beverage container, wherein a bottom surface of the arm at least partially comprises a layer transparent to ultraviolet light.

2. The apparatus according to claim 1, wherein the at least one sensor is configured to verify the identity of a user based upon biometric data,
wherein the biometric data comprises one or more of user breath, user saliva, at least one fingerprint, at least one retina scan, and at least one DNA test.

3. The apparatus according to claim 1, wherein the at least one sensor is configured to detect that the lid has been removed from the beverage container.

4. The apparatus according to claim 1, wherein the apparatus further comprises at least one display and is configured to:
receive at least one sample of saliva or breath;
detect at least one disease present in the at least one sample; and
display the results.

5. The apparatus according to claim 1, wherein the at least one sensor is configured to test the atmosphere for at least one predetermined substance,
wherein the at least one predetermined substance comprises at least carbon monoxide.

6. The apparatus according to claim 1, wherein the apparatus further comprises a wireless charging interface.

7. The apparatus according to claim 1, wherein the at least one sensor is configured to perform at least one of voiceprint analysis and other voice recognition mechanism.

8. The apparatus according to claim 1, wherein the apparatus further comprises at least one radio frequency identification (RFID) tag.

9. The apparatus according to claim 1, wherein the apparatus is configured to permit commercial transactions and further comprises at least one of a credit card reader, magnetic strip reader, and chip reader.

10. The apparatus according to claim 1, wherein the apparatus further comprises at least one camera mounted to a top surface of the apparatus configured to:
take at least one panoramic or semi-spherical picture; and
tag the at least one picture with at least one description of at least one food or drink.

11. The apparatus according to claim 1, wherein the apparatus further comprises at least one transceiver configured to communicate with a remote server to determine whether charges to, or withdrawals from, a credit card, debit card, or gift card are authorized.

12. An apparatus, comprising:
a cover;
a cover portion extending in a direction orthogonal to the cover,
wherein the cover is joined to the cover portion at a circumferential edge of the cover to cover a beverage container, and
wherein the lid comprises at least one user interface; and
an arm extending in a direction orthogonal to the lid from a central portion of the lid and configured to supply ultraviolet light to contents of the beverage container,
wherein a bottom surface of the arm at least partially comprises a layer transparent to ultraviolet light.

13. The apparatus according to claim 1, wherein the lid is configured to display light from a generally planar section via optical fibers or mirrors.

14. The apparatus according to claim 1, wherein the lid further comprises at least one transceiver configured to communicate with an application configured to summon a taxi or stream video data over an Internet connection.

15. The apparatus according to claim 1, wherein the lid further comprises at least one timer connected to a display to show an indication of how long the lid has been used, the time of day, or the time until a restaurant or bar associated with the lid closes or stops serving alcoholic drinks.

16. The apparatus according to claim 1, wherein the lid further comprises at least one power storage device connected to an electronic display.

17. The apparatus according to claim 1, wherein the lid further comprises at least one user interface disposed on top of the lid, around an edge of the lid, or on underside of the lid.

18. The apparatus according to claim 1, wherein the lid comprises at least one sterilizer configured to project light comprising a three-dimensional holographic projection.

19. The apparatus according to claim 1, wherein the lid comprises at least one battery coupled with a wireless charging interface.

20. The apparatus according to claim 1, wherein the lid comprises at least one speaker configured to emit an audible alarm.

21. An apparatus, comprising:
a lid comprising at least one interactive display integral to the lid; and
a lip portion extending in a direction orthogonal to the lid,
wherein the lid is joined to the lip portion at a circumferential edge of the lid to form a cover for a beverage container, and
wherein the lid comprises at least one user interface; and
an arm extending in a direction orthogonal to the lid from a central portion of the lid and configured to supply ultraviolet light to contents of the beverage container,
wherein a bottom surface of the arm at least partially comprises a layer transparent to ultraviolet light.

22. The apparatus according to claim 21, wherein the apparatus further comprises at least one of:
a top surface comprising an erasable, re-writable surface, and
a touch-sensitive user interface.

23. The apparatus according to claim 21, wherein the apparatus further comprises communications hardware configured to permit the user to access the internet.

24. The apparatus according to claim 21, wherein the at least one interactive display is configured to display at least one advertisement based on at least one of a number of drinks consumed and a duration of time that the lid is in use.

25. The apparatus according to claim 21, wherein the at least one interactive display is configured to locate other similar peer devices.

26. The apparatus according to claim 21, wherein the at least one interactive display is configured to at least one of accept music requests and transmit at least one music request to a jukebox system or to a live band.

27. An apparatus, comprising:
a lid;
a lip portion extending in a direction orthogonal to the lid,
wherein the lid is joined to the lip portion at a circumferential edge of the lid to form a cover for a beverage container, and
wherein the lid comprises at least one user interface; and
an arm extending in a direction orthogonal to the lid from a central portion of the lid and configured to supply ultraviolet light to contents of the beverage container,
wherein a bottom surface of the arm at least partially comprises a layer transparent to ultraviolet light.

28. The apparatus according to claim 27, wherein the lid comprises at least one vibration mechanism integral to the lid, and wherein the at least one vibration mechanism is configured to stimulate the contents of the beverage container.

29. The apparatus according to claim 27, wherein the lid comprises at least one vibration mechanism integral to the lid, and wherein the at least one vibration mechanism is configured to at least one of add air to wine and mix contents of a beverage glass or disposable cup.

* * * * *